United States Patent [19]

Kurono et al.

[11] Patent Number: 4,824,855

[45] Date of Patent: Apr. 25, 1989

[54] 1,4-DIHYDROPYRIDINE DERIVATIVES

[75] Inventors: Masayasu Kurono, Mie; Tsunemasa Suzuki, Matsubase; Yasuaki Kondo; Kenji Hamase, both of Kasugai; Toshinao Usui, Gifu; Tomoo Suzuki, Kasugai; Masato Fukushima, Komaki; Kiichi Sawai, Funabashi, all of Japan

[73] Assignee: Sanwa Kagaku Kenkyusho Co., Ltd., Aichi, Japan

[21] Appl. No.: 119,227

[22] Filed: Nov. 5, 1987

Related U.S. Application Data

[63] Continuation-in-part of Ser. No. 921,080, Oct. 21, 1986, abandoned.

[30] Foreign Application Priority Data

Oct. 22, 1985 [JP] Japan .................. 60-234449
Jun. 24, 1986 [JP] Japan .................. 61-146030

[51] Int. Cl.$^4$ .................. A61K 31/455; C07D 211/86
[52] U.S. Cl. ...................... 514/356; 546/321; 546/14; 546/273; 514/339
[58] Field of Search .............. 546/14, 194, 275, 281, 546/321; 540/597; 514/210, 212, 318, 340, 343, 356

[56] References Cited

U.S. PATENT DOCUMENTS 3,996,234 12/1976 Bossert et al. .............. 546/321
4,048,171 9/1977 Bosset et al. ............... 546/321
4,652,573 3/1987 Minaskanian et al. ......... 546/187

FOREIGN PATENT DOCUMENTS 31663 2/1982 Japan ....................... 546/321

OTHER PUBLICATIONS

Iwanami et al., Chem. Pharm. Bull. vol. 27, pp. 1426–1440 (1979).

Primary Examiner—Jane T. Fan
Attorney, Agent, or Firm—Armstrong, Nikaido, Marmelstein, Kubovcik & Murray

[57] ABSTRACT

1,4-Dihydropyridine derivatives represented by the formula

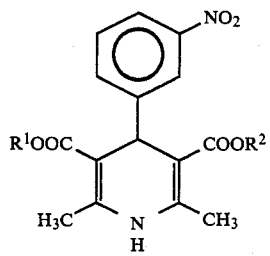

wherein one of $R^1$ and $R^2$ is cycloalkylmethyl group and the other is a group of

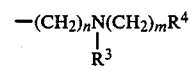

in which $R^3$ is hydrogen atom or lower alkyl group and $R^4$ is hydrogen atom, hydroxyl radical, carboxyl radical, alkoxycarbonyl group, carbamoyl radical, phenyl radical, substituted phenyl radical or trialkylsilyl group, or $R^3$ and $R^4$ may be bonded each other, and n and m are an integer of 1 to 6, respectively salts thereof, a process for the preparation of same as well as a pharmaceutical agent comprising the compound or salt, as an effective ingredient.

10 Claims, No Drawings

1,4-DIHYDROPYRIDINE DERIVATIVES

This application is a continuation-in-part of application Ser. No. 921,080 filed Oct. 21, 1986, now abandoned.

BACKGROUND OF THE INVENTION

1. Field of the Invention

The present invention relates to 1,4-dihydropyridine derivatives, salts thereof, a process for the preparation of same as well as a pharmaceutical agent comprising at least one of the compounds and salts, as an effective ingredient.

2. Related Arts

It has been know that certain kind 1,4-dihydropyridine derivatives have a powerful calcium antagonistic effect and thus can be employed as an effective ingredient for curing blood circulatory diseases.

As one of exemplar known 1,4-dihydropyridine derivatives, dimethyl ester of 1,4-dihydro-2,6-dimethyl-4-(2-nitropheny)pyridine-3,5-dicarboxylic acid (known as —Nifedipine—) may be listed. This compound has pharmaceutical activities of coronary vasodilating action, blood pressure depressing action and the like [W. Vater et al "Arzneim.-Forsch" (Drug Res.), Vol. 22, page 1, 1972]. As another exemplar known compound, 1,4-dihydro-2,6-dimethyl-4-(3-nitrophenyl)-pyridine-3,5-dicarboxylic acid 3-2-(N-benzyl-N-methylamino)ethyl 5-methyl ester (known as —Nicardipine—) may be listed, which has a cerebral blood flow increasing action.

Among the both known compounds, the Nifedipine shows a powerful depressing action but as a result, has a tendency of causing a relative decrease on cerebral blood flow. On the other hand, the Nicardipine having the cerebral blood flow increasing action, has been developed and clinically employed as one of cerebral circulation improving agents but it can not be said as it selectively acts to the cerebral blood path to increase only the blood flow therein.

SUMMARY OF THE INVENTION

A principal object of the present invention is to provide novel 1,4-dihydropyridine derivatives and salts thereof, each of which has an excellent Ca antagonistic effect and acts selectively to cerebral blood path to show a powerful cerebral blood flow increasing action.

Additional objects of the invention are to provide a process for the preparation of the compounds and salts as well as a pharmaceutical agent comprising at least one of the compounds or salts, as an effective ingredient, respectively.

According to the invention, the principal object is attained by a 1,4-dihydropyridine derivative represented by the formula

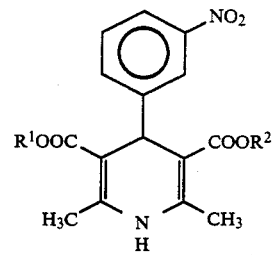

wherein one of $R^1$ and $R^2$ is cycloalkylmethyl group and the other is a group of

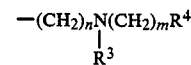

in which $R^3$ is hydrogen atom or loweer alkyl group and $R^4$ is hydrogen atom, hydroxyl radical, carboxyl radical, alkoxycarbonyl group, carbamoyl radical, phenyl radical, substituted phenyl radical or trialkylsilyl group, or $R^3$ and $R^4$ may be bonded each other, and n and m are an integer of 1 to 6, respectively or a salt thereof.

In the compound as shown by Formula I, cyclopropylmethyl, cyclobutylmethyl, cyclopentylmethyl and cyclohexylmethyl radicals may be listed as the exemplar cycloalkylmethyl group. As examples for the lower alkyl group, methyl, ethyl and propyl radicals may be listed. As examples for the substituted phenyl radical, 2-chlorophenyl, 4-chlorophenyl, 4-bromophenyl, 4-fluorophenyl, 4-methoxyphenyl, 4-nitophenyl and 2,4-dichlorophenyl radicals may be listed. As examples for the trialkylsilyl group, trimethylsiyl, triethylsilyl and t-butyldimethylsilyl radicals may be listed. When the substituents $R^3$ and $R^4$ bond each other, a heterocyclic ring is formed together with the nitrogen atom neiboughring to the substituent $R^3$. As examples for the heterocyclic ring, 1-pyrrolidinyl, 1-piperidinyl, 2-isoindolinyl and 2-(5-chloroisoindolinyl) radicals may be listed.

According to the process of the invention, the compounds (I) and salts thereof can be prepared by reacting in the presence of ammonia or a salt thereof, a compound represented by the formula

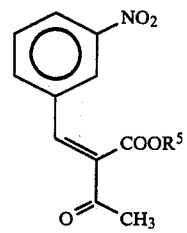

wherein $R^5$ is cycloalkylmethyl group or a group of

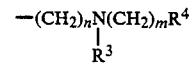

in which $R^3$, $R^4$, n and m have the meanings as referred to with a compound represented by the formula

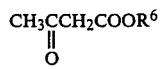 (III)

wherein $R^6$ is cycloalkylmethyl group or a group of

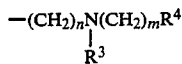

in which $R^3$, $R^4$, n and m have the meanings as referred to but $R^6$ in this compound (III) and $R^5$ in the compound (II) do not have same meaning of the cycloalkylmethyl group or the group of

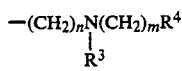

in which $R^3$, $R^4$, n and m have the meanings as referred to and if necessary, converting the resulting reaction product into the salt.

A molar ratio of 1:0.8 to 1:1.5 is preferable for the raw material compounds II and III. The reaction can be carried out at 50° to 150° C., in the presence or absence of a solvent. As the solvent, alcohols such as methanol, ethanol, isopropanol and the like; aromatic hydrocarbons such as benzene, toluene and the like; aprotic polar solvents such as dimethylformamide and the like; ethers such as ethylether, tetrahydrofuran and the like; or water can be employed. An isolation of the objective compound from the reaction mixture can be carried out through operations known per se, such as concentration, extraction, column chromatography, recrystallization and the like.

The benzylidenes (II) as one of the raw materials may be of those obtained from a market and otherwise, those can be synthesized through a condensation reaction between the aldehyde represented by the formula

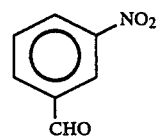 (IV)

and said ester shown by Formula III, in accordance with the method as disclosed by G. Jones in "Org. Reactions" Vol. 15, page 204, 1967. The ester (III) as the other raw material may also be of commercially available one and otherwise, those can be synthesized in accordance with the method as disclosed by Oren-Olov Lawesson et al in "Org. Syn." Vol. V, page 155, 1973.

As referred to before, the ammonia or a salt thereof is employed when the compounds (I) will be synthesized, and as examples for the ammonium salt, ammonium acetate, ammonium carbonate and ammonium hydrogen carbonate may be listed.

The compounds shown by Formula I may be synthesized through various routes other than that as referred to and thus some of which are explained below, for mere references.

Route A

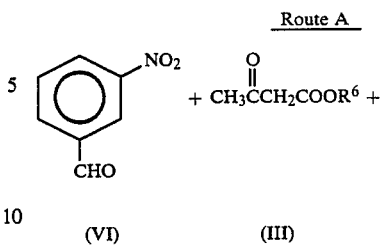

(VI)    (III)

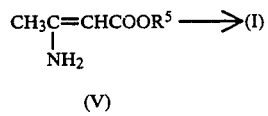

(V)

wherein $R^5$ and $R^6$ have the meanings as referred to.

The synthetic reaction for this route can be carried out in accordance with a method similar to that as disclosed by H. H. Fox et al in "J. Org. Chem." Vol. 16, page 1259, 1951. A molar ratio of 1:0.8:0.8 to 1:1.5:1.5 is preferable for the raw materials, and in this case, reaction conditions, solvent and operation manners are substantially same with the method as described before for the process according to the invention.

The aldehyde shown by Formula IV can be commercially obtained, and as to the ester (III), please refer to the disclosure given before for the process according to the invention. The enaminoester shown by Formula V may also be obtained from a market and otherwise, can be synthesized in accordance with the method as disclosed, for instance by S. A. Glickman and A. C. Cope in "J. Am. Chem. Soc." Vol. 67, page 1017, 1945.

Route B

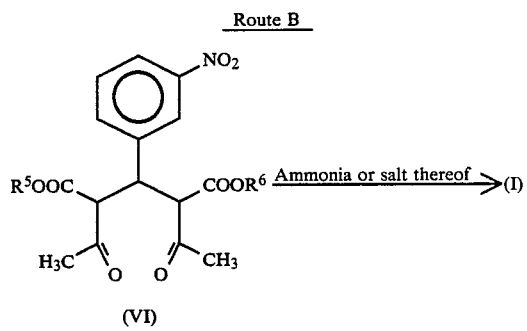

(VI)

wherein $R^5$ and $R^6$ have the meanings as referred to.

This synthetic route is similar to that as disclosed by A. Singer and S. M. McElvain in "Org. Syn." Vol. II, page 214, 1943. In this case, the reaction conditions, solvent and reaction operations are substantially same with those as described before for the process accordting to the invention.

The diketoesters shown by Formula VI may be of those available from a market and otherwise can be synthesized in accordance with the manner as disclosed by G. Jones in "Org. Reactions" Vol. 15, page 204, 1967 and with use of the compound shown by Formula II and a catalyst of potassium fluoride, cesium fluoride or the like.

Route C

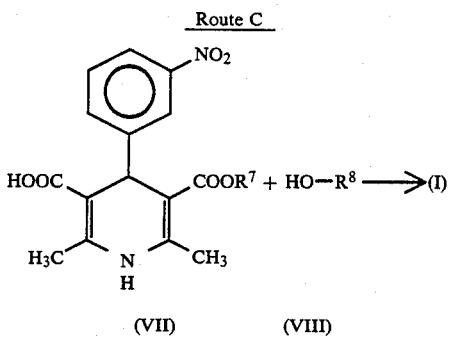

wherein R⁷ is cycloalkylmethyl group and R⁸ is a group of

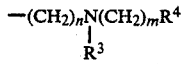

in which $R^3$, $R^4$, n and m have the meanings as referred to.

This synthetic route is similar to that as disclosed by T. Shibanuma et al in "Chem. Pharm. Bull." Vol. 28, page 2809, 1980. The carboxylic acids shown by Formula VII may be of those available from a market and otherwise, can be synthesized in accordance with the manner as disclosed in the literature.

In accordance with this route, the raw material (VII) is reacted firstly with thionyl chloride, phosphorus pentachloride or chloroformic ethyl ester in same molar amount, in the presence of a solvent such as methylene chloride, chloroform or the like halogenated hydrocarbons, benzene, toluene or the like aromatic hydrocarbons, diethyl ether, tetrahydrofuran, dimethoxyethane, dioxane or the like ethers, dimethylformamide or the like aprotic polar solvents or a mixture thereof and then reacted with the alcohol (VIII) in same molar amount. Otherwise, the compounds (I) may be prepared by composing the both raw materials in same molar amount, adding therein dicyclohexylcarbodiimido in same molar amount and then reacting the materials in a solvent in the presence of N,N-dimethylaminopyridine in a catalystic amount.

Even if any of the synthetic methods is selected for this route C, an isolation of the objective compound can be attained in the manner similar to that as dislosed before for the process according to the invention.

EFFECTS OR ADVANTAGES OF THE INVENTION

The 1,4-dihydropyridine derivatives and salts thereof according to the invention show an excellent Ca antagonistic effect and selectively act to cerebral blood path to show a remarkable cerebral blood flow increase and thus those are preferable to use as an effective ingredient for cerebral circulation improving agents.

On the other hand, the process according to the invention has an advantage that such useful compounds can be prepared in relatively easy manner by starting from raw materials which are easy available from a market or can easily be synthesized.

FORM AND AMOUNT FOR DOSAGE AS PHARMACEUTICAL AGENT

Each of the compounds and salts according to the invention can be made with conventional additives or carriers into a tablet, capsul, granule or the like form for oral dosage.

A dosing amount of the compound or salt for human depends on kind of the compound to be used, selected medicine form, condition of illness, age of a patient and other factors but in case for an adult, 1 to 100 mg/day is generally preferable.

DETAILED DESCRIPTION OF PREFERRED EMBODIMENTS

The invention will now be further explained with reference to Examples, Pharmaceutical Test Examples and Prescriptional Examples.

EXAMPLE 1

A mixture of 4.0 g (16 mmol) of 2-(N-benzyl-N-methylamino)ethyl acetoacetate, 4.6 g (16 mmol) of cyclopropylmethyl 2-(3-nitrobenzylidene)acetoacetate, 1.12 ml of 28% aqueous ammonia and 40 ml of ethanol was stirred at the reflux temperature for 8 hours, and then the solvent was removed under reduced pressure. The residue was chromatographed on silica gel column to afford 3-cyclopropylmethyl 5-[2-(N-benzyl-N-methylamino)ethyl] 1,4-dihydro-2,6-dimethyl-4-(3-nitrophenyl)pyridine-3,5-dicarboxylate (3.5 g, 42.1%) as yellow oil. Treatment of this oil with hydrochloric acid gave the corresponding salt.

| $^1H$—NMR spectrum (CDCl₃)δ ppm: | |
| --- | --- |
| 0.10–1.37 | (5H, m) |
| 2.37 | (3H, s) |
| 2.43 | (3H, s) |
| 2.66 | (3H, s) |
| 3.23–3.57 | (2H, m) |
| 3.87 | (2H, d) |
| 4.37 | (2H, s) |
| 4.33–4.70 | (2H, m) |
| 5.11 | (1H, s) |
| 7.43–8.20 | (9H, m) |
| 9.56 | (1H, s) |
| 11.70 | (1H, brs) |

Mass spectrum (EI/DI) m/z: 519 (M+), 148, 134 (base peak).

Elementrary analysis ($C_{29}H_{33}N_3O_6 \cdot HCl \cdot 1/2H_2O$): Cal.; H 6.24, C 61.64, N 7.43. Found; H 6.26, C 61.76, N 7.33.

EXAMPLE 2

A mixture of 13.0 g (75 mmol) of 2-(N,N-dimethylamino)ethyl acetoacetate, 21.7 g (75 mmol) of cyclopropylmethyl 2-(3-nitrobenzylidene)-acetoacetate, 6.0 ml of 28% aqueous ammonia and 70 ml of ethanol was stirred at the reflux temperature for 7 hours, and then the solvent was removed under reduced pressure. The residue was chromatographed on silica gel column and crystallized from ethyl ether to afford 3-cyclopropylmethyl 5-[2-(N,N-dimethylamino)ethyl] 1,4-dihydro-2,6-dimethyl-4-(3-nitrophenyl)pyridine-3,5-dicarboxylate (14.1 g, 42.3%) as yellow crystals.

| $^1H$—NMR spectrum (CDCl₃)δ ppm: | |
| --- | --- |
| 0.00–1.50 | (5H, m) |
| 2.27 | (6H, s) |
| 2.30 | (6H, s) |
| 2.57 | (2H, t) |
| 3.92 | (2H, d) |
| 4.19 | (2H, t) |

-continued

| $^1$H—NMR spectrum (CDCl$_3$)δ ppm: | |
|---|---|
| 5.22 | (1H, s) |
| 6.30 | (1H, s) |
| 7.30–8.30 | (4H, m) |

Mass spectrum (EI/DI) m/z: 443 (M$^+$), 71 (base peak).

Elementrary analysis (C$_{23}$H$_{29}$N$_3$O$_6$): Cal.; H 6.59, C 62.27, N 9.47. Found; H 6.63, C 62.08, N 9.47.

Melting point: 125°–126° C.

EXAMPLE 3

A mixture of 10.0 g (35 mmol) of 2-[N-(4-chlorobenzyl)-N-methylamino]-ethyl acetoacetate, 10.2 g (35 mmol) of cyclopropylmethyl 2-(3-nitrobenzylidene)acetoacetate, 2.9 ml of 28% aqueous ammonia and 50 ml of ethanol was stirred at the reflux temperature for 7 hours, and then the solvent was removed under reduced pressure. The residue was chromatographed on silica gel column and crystallized from methanol to afford 3-[2-[N-(4-chlorobenzyl)-N-methylamino]ethyl] 5-cyclopropylmethyl 1,4-dihydro-2,6-dimethyl-4-(3-nitrophenyl)pyridine-3,5-dicarboxylate (11.0 g, 56.3%) as yellow crystals.

| $^1$H—NMR spectrum (CDCl$_3$)δ ppm: | |
|---|---|
| 0.00–1.33 | (5H, m) |
| 2.16 | (3H, s) |
| 2.37 | (6H, s) |
| 2.58 | (2H, t) |
| 3.43 | (2H, s) |
| 3.86 | (2H, d) |
| 4.16 | (2H, t) |
| 5.16 | (1H, s) |
| 6.13 | (1H, brs) |
| 7.20–8.30 | (8H, m) |

Mass spectrum (EI/DI) m/z: 553 (M$^+$), 181 (base peak).

Elementrary analysis (C$_{29}$H$_{32}$ClN$_3$O$_6$): Cal.; H 5.82, C 62.85, N 7.58. Found; H 5.90, C 62.52, N 7.53.

Melting point: 115°–116.5° C.

EXAMPLE 4

A mixture of 8.8 g (30 mmol) of 2-[N-(4-methoxybenzyl)-N-methylamino]-ethyl acetoacetate, 8.5 g (30 mmol) of cyclopropylmethyl 2-(3-nitrobenzylidene)acetoacetate, 2.5 ml of 28% aqueous ammonia and 50 ml of ethanol was stirred at the reflux temperature for 7 hours, and then the solvent was removed under reduced pressure. The residue was chromatographed on silica gel column to afford 3-cyclopropylmethyl 5-[2-[N-(4-methoxybenzyl)-N-methylamino]ethyl] 1,4-dihydro-2,6-dimethyl-4-(3-nitrophenyl)pyridine-3,5-dicarboxylate (7.8 g, 46.7%) as yellow oil. Treatment of this oil with 1 equivalent of fumaric acid in ethanol gave the corresponding fumarate.

| $^1$H—NMR spectrum (DMSO-d$_6$)δ ppm: | |
|---|---|
| 0.00–1.50 | (5H, m) |
| 2.16 | (3H, s) |
| 2.34 | (6H, s) |
| 2.40–2.90 | (2H, m) |
| 3.53 | (2H, s) |
| 3.77 | (3H, s) |
| 3.85 | (2H, d) |
| 4.16 | (2H, t) |
| 5.12 | (1H, s) |
| 6.71 | (2H, s) |
| 6.93 | (2H, d) |
| 7.24 | (2H, d) |
| 7.35–8.25 | (4H, m) |
| 8.13 | (1H, brs) |

Mass sepctrum (EI/DI) m/z: 549 (M$^+$), 177 (base peak).

Elementrary analysis (C$_{34}$H$_{39}$N$_3$O$_{11}$.1/2H$_2$O). Cal.; H 6.12, C 60.43, N 6.22. Found; H 6.00, C 60.48, N 6.22.

Melting point: 118°–130° C.

EXAMPLE 5

A mixture of 15.3 g (53 mmol) of 2-(N-methyl-N-trimethylsilylmethylamino)ethyl acetoacetate, 13.0 g (53 mmol) of cyclopropylmethyl 2-(3-nitrobenzylidene)acetoacetate, 4.4 ml of 28% aqueous ammonia and 50 ml of ethanol was stirred at the reflux temperature for 7 hours, and then the solvent was removed under reduced pressure. The residue was chromatographed on silica gel column to afford 3-cyclopropylmethyl 5-[2-(N-methyl-N-trimethylsilylmethylamino)ethyl] 1,4-dihydro-2,6-dimethyl-4-(3-nitrophenyl)pyridine-3,5-dicarboxylate (7.0 g, 25.7%) as yellow oil. Treatment of this oil with 1 equivalent of fumaric acid in ethanol gave the corresponding fumarate.

| $^1$H—NMR spectrum (DMSO-d$_6$)δ ppm: | |
|---|---|
| 0.00 | (9H, s) |
| 0.03–1.50 | (5H, m) |
| 2.13 | (2H, s) |
| 2.33 | (9H, s) |
| 2.77 | (2H, t) |
| 3.80 | (2H, d) |
| 5.05 | (1H, s) |
| 6.65 | (2H, s) |
| 7.50–8.25 | (4H, m) |
| 9.09 | (1H, brs) |

Mass sepctrum (EI/DI) m/z: 515 (M$^+$), 130 (base peak).

Elementrary analysis (C$_{30}$H$_{41}$N$_3$O$_{10}$Si.1/2H$_2$O). Cal.; H 6.61, C 56.23, N 6.56. Found; H 6.64, C 56.38, N 6.30.

Melting point: 73°–76° C.

EXAMPLE 6

A mixture of 6.57 g (30.4 mmol) of 2-(N-carbamoylmethyl-N-methylamino)ethyl acetoacetate, 8.79 g (30.4 mmol) of cyclopropylmethyl 2-(3-nitrobenzylidene)acetoacetate, 2.4 ml of 28% aqueous ammonia and 30 ml of ethanol was stirred at the reflux temperature for 7 hours, and then the solvent was removed under reduced pressure. The residue was chromatographed on silica gel column and crystallized from ethylether to afford 3-[2-N-carbamoylmethyl-N-methylamino)ethyl 5-cyclopropylmethyl 1,4-dihydro-2,6-dimethyl-4-(3-nitrophenyl)pyridine-3,5-dicarboxylate (8.67 g, 58.7%) as yellow crystals.

| $^1$H—NMR spectrum (CDCl$_3$ + DMSO-d$_6$)δ ppm: | |
|---|---|
| 0.00–1.40 | (5H, m) |
| 2.31 | (3H, s) |
| 2.38 | (6H, s) |
| 2.67 | (2H, t) |

-continued

| $^1$H—NMR spectrum (CDCl$_3$ + DMSO-d$_6$)δ ppm: | |
|---|---|
| 2.98 | (2H, s) |
| 3.87 | (2H, d) |
| 4.19 | (2H, t) |
| 5.16 | (1H, s) |
| 7.03 | (2H, brs) |
| 7.38–8.30 | (4H, m) |
| 8.92 | (1H, brs) |

Mass spectrum (EI/DI) m/z: 486 (M+), 469 (base peak).

Elementrary analysis (C$_{24}$H$_{30}$N$_4$O$_7$). Cal.; H 6.21, C 59.22, N 11.51. Found; H 6.52, C 59.07, N 11.46.

Melting point: 176°–178° C.

EXAMPLE 7

A mixture of 15.1 g (47.05 mmol) of 2-[N-(2,4-dichlorobenzyl)-N-methyl-amino]ethyl acetoacetate, 13.7 g (47.4 mmol) of cyclopropylmethyl 2-(3-nitrobenzylidene)acetoacetate, 3.4 ml of 28% aqueous ammonia and 70 ml of ethanol was stirred at the reflux temperature for 7 hours, and then the solvent was removed under reduced pressure.

The residue was chromatographed on silica gel column to afford the desired compound as yellow oil. Treatment of this oil with hydrochloric acid gave the corresponding salt.

| $^1$H—NMR spectrum (DMSO-d$_6$)δ ppm: | |
|---|---|
| 0.00–1.40 | (5H, m) |
| 2.33 | (3H, s) |
| 2.41 | (3H, s) |
| 2.69 | (3H, s) |
| 3.35–3.70 | (2H, m) |
| 3.87 | (2H, d) |
| 4.27–4.67 | (2H, m) |
| 5.10 | (1H, s) |
| 7.47–8.23 | (2H, m) |
| 9.48 | (1H, brs) |

Mass spectrum (EI/DI) m/z: 587 (M+), 180 (base peak).

Elementary analysis (C$_{29}$H$_{31}$Cl$_2$N$_3$O$_6$.H$_2$O): Cal.; H 5.33, C 54.17, N 6.54. Found; 5.08, C 53.93, N 6.53.

Melting point: 95°–101° C.

EXAMPLE 8

A mixture of 9.95 g (35.4 mmol) of 2-(5-chloroisoindolin-2-yl)ethyl acetoacetate, 10.2 g (35.3 mmol) of cyclopropylmethyl 2-(3-nitro-benzylidene)acetoacetate, 2.61 ml of 28% aqueous ammonia and 60 ml of ethanol was stirred at the reflux temperature for 7 hours, and then the solvent was removed under reduced pressure.

The residue was chromatographed on silica gel column and crystallized from methanol to afford the desired compound as yellow crystals.

| $^1$H—NMR spectrum (CDCl$_3$)δ ppm: | |
|---|---|
| 0.00–1.37 | (5H, m) |
| 2.38 | (6H, s) |
| 2.96 | (2H, t) |
| 3.88 | (2H, d) |
| 3.92 | (4H, s) |
| 4.25 | (2H, t) |
| 5.20 | (1H, s) |
| 6.03 | (1H, brs) |
| 7.13–8.23 | (7H, m) |

Mass spectrum (EI/DI) m/z: 551 (M+), 189 (base peak).

Elementary analysis (C$_{29}$H$_{30}$ClN$_3$O$_6$): Cal.; H 5.48, C 63.10, N 7.61. Found; H 5.49, C 62.81, N 7.54.

Melting point: 145°–148° C.

PHARMACEUTICAL TEST EXAMPLE 1

(Ca Antagonistic Effect)

Ca antagonistic effect was examined on a spiral strip of New Zealand white rabbit aorta with the Magnus method. The response of preparations was recorded isometically on a recorder. Contraction induced Ca (25 mM) after K depolarization in Ca free solution was compared with a compound or not.

The data given in following Table 1 are presented as inhibitory % to concentration without the compound.

TABLE 1

| Compound | Concentration (mol) | Number of head | Inhibitory (%) Concentration of Ca ion | |
|---|---|---|---|---|
| | | | 2.5 mM | 5.0 mM |
| Test | | | | |
| Example 1 | 10$^{-7}$ | 6 | 94.7 ± 3.72 | >100 |
| Example 1 | 10$^{-8}$ | 5 | 76.1 ± 6.62 | 81.3 ± 5.46 |
| Control | | | | |
| Nifedipine | 10$^{-7}$ | 5 | >100 | >100 |
| Nifedipine | 10$^{-8}$ | 5 | 63.5 ± 7.33 | 62.3 ± 7.91 |
| Nicardipine | 10$^{-7}$ | 5 | 90.9 ± 12.06 | 83.2 ± 15.93 |
| Nicardipine | 10$^{-8}$ | 5 | 26.5 ± 18.40 | 16.3 ± 21.28 |

PHARMACEUTICAL TEST EXAMPLE 2

(Negative inotropic effect)

New Zealand white rabbit was killed by bleeding from the carotid artery and the left atrium was quickly removed. The left atrium was suspended in an organ bath where Tyrode's solution was kept at 37° C. and bubbled with a gas mixture of 95% O$_2$–5% CO$_2$, and the atrium was drived electric stimulation (1 Hz, 2 msec, 10 V). The response of preparations was recorded isometically on a recorder. The initial tension applied to the preparation was adjusted to 1 g.

Results are shown in following Table 2.

TABLE 2

| Compound | Change (%) Concentration of the compound (mol) | | | ID$_{50}$ (× 10$^{-4}$) |
|---|---|---|---|---|
| | 10$^{-6}$ | 10$^{-5}$ | 10$^{-4}$ | |
| Test | | | | |
| Example 1 | NE | −7.4 | −15.7 | 3.2 |
| Control | | | | |
| Nifedipine | NE | −9.5 | −19.0 | 1.2 |
| Nicardipine | −3.4 | −13.5 | −25.6 | 0.34 |

In the Table, NE: not effective which means that no notifiable change is recorded.

PHARMACEUTICAL TEST EXAMPLE 3

(Effect of compounds on vertebral and femoral arterial blood flow)

An experiment was carried out by anesthetizing adult male and female mongrel dogs (weight; 10–20 kg) with Nembutal (30 mg/kg i.p.) and artificially respiring (20 ml/kg/stroke, 20 strokes/min) the animals.

from administration, to obtain the results shown in Table 5 below:

TABLE 5

| Compound | Dose (mg/kg) | N | Pre-value | 1 hr | 2 hr | 4 hr | 6 hr | 24 hr |
| --- | --- | --- | --- | --- | --- | --- | --- | --- |
| No compound | — | 6 | 214 ± 2.5 | 0.1 ± 1.25 | 0.7 ± 1.12 | 4.3 ± 1.55 | −1.4 ± 2.94 | −3.3 ± 1.14 |
| Testing | | | | | | | | |
| a | 3.0 | 9 | 226 ± 4.1 | −10.0 ± 4.06 | −7.7 ± 4.43 | −15.6 ± 4.83 | −14.0 ± 2.79 | −9.9 ± 3.82 |
| c | 3.0 | 6 | 214 ± 3.0 | −7.6 ± 2.51 | −10.2 ± 3.69 | −12.6 ± 4.26 | −9.5 ± 2.85 | −10.7 ± 4.36 |
| g | 3.0 | 6 | 220 ± 2.4 | −33.3 ± 6.57 | −35.2 ± 4.12 | −34.0 ± 2.42 | −32.8 ± 2.72 | −13.0 ± 5.94 |
| h | 3.0 | 6 | 217 ± 3.1 | −3.0 ± 1.47 | −9.0 ± 2.82 | −13.2 ± 6.15 | −21.4 ± 3.67 | −14.3 ± 4.09 |
| Control | | | | | | | | |
| Nifedipine | 3.0 | 6 | 218 ± 3.0 | −19.3 ± 4.41 | −10.6 ± 3.14 | −4.3 ± 2.70 | −0.1 ± 1.56 | −1.1 ± 1.06 |
| Nicardipine | 3.0 | 6 | 222 ± 1.8 | −10.0 ± 2.28 | −5.7 ± 1.61 | −3.0 ± 2.01 | −1.0 ± 1.50 | −4.2 ± 1.88 |

Right vertebral and femoral arteries were exposed and each probe of electro-magnetic flow meter was fitted therein to measure vertebral and femoral arterial blood flow. A cannula was inserted into descending aorta from left femoral artery in order to measure blood pressure by pressure transducer connected to amplifier. Each of test compounds dissolved in 50% ethanol solution (1 μg/kg, i.v.) was administered from the cannula into cephlic vein.

Results of change in blood flow and blood pressure are given in following Table 3.

TABLE 3

| Compound | Number of head | Change (%) | | |
| --- | --- | --- | --- | --- |
| | | VABF | FABF | DBP |
| Test | | | | |
| Example 1 | 6 | 51 ± 13 | 25 ± 8 | −9 ± 1 |
| Example 3 | 6 | 56 ± 12 | 23 ± 8 | −8 ± 1 |
| Example 4 | 6 | 33 ± 5 | 19 ± 6 | −6 ± 1 |
| Control | | | | |
| Nicardipine | 5 | 32 ± 7 | 14 ± 5 | −10 ± 1 |

In the Table,
VABF: vertical arterial blood flow,
FABF: femoral arterial blood flow, and
DBP: diastolic blood pressure.

PHARMACEUTICAL TEST EXAMPLE 4

(Acute toxicity)

Male and female dd mice were used (weight: 18–20 g). Each of compounds to be tested was dissolved in 1% Nikkol and administered directly into stomach by forced oral administration and with use of a metal sonde. $LD_{50}$ of the compounds were calculated by Litchfield-Wilcoxon method, after observation for 72 hours.

Results are shown in following Table 4.

TABLE 4

| Compound | $LD_{50}$ (mg/kg) |
| --- | --- |
| Test | |
| Example 1 | 211 |
| Control | |
| Nicardipine | 305 |

PHARMACEUTICAL TEST EXAMPLE 5

(Blood pressure depressing action)

The testing or control compound was orally administered to the indicated number (N) of spontaneously hypertensive male rats (15 or more weeks old). Measurement of the systolic pressure (mm Hg) in the median sacral artery was made at 1, 2, 4, 6 and 24 hours

PHARMACEUTICAL TEST EXAMPLE 6

(Vertebral and femoral arterial blood flow increasing action)

The bloodflow increasing action of the compounds was measured on anesthetized dogs, in a manner similar to that of Pharmaceutical Test Example 3, to obtain the results shown in Table 6 below:

TABLE 6

| Compounds | $ED_{50}$ (μg/kg) i.v. |
| --- | --- |
| Testing | |
| a | 1.7 |
| b | 3.8 |
| c | 1.1 |
| d | 1.4 |
| e | 3.1 |
| f | 2.6 |
| g | 1.1 |
| h | 1.6 |
| Control | |
| Nicardipine | 4.2 |

$ED_{50}$ in the Table indicates the amount of the compound required to increase the vertebral arterial blood flow by 50%.

From the data given in Tables 5 and 6, it can be concluded that (a) the compounds according to the present invention exhibit blood pressure suppressing action over an extended time period, as compared to the conventional compounds Nifedipine and Nicardipine, and (b) the compounds according to the present invention are superior in vertebral arterial blood flow increasing action than Nicardipine, a compound known to exhibit high cerebral blood flow increasing action.

PRESCRIPTIONAL EXAMPLE 1 (TABLET)

Following components were mixed to prepare tablets in a conventional manner.

| Compound of Example 1 | 1 (mg) |
| --- | --- |
| Potato starch | 60 |
| Fine crystalline cellulose | 30 |
| Geratin | 8 |
| Magnesium stearate | 1 |
| | 100 (mg/tablet) |

PRESCRIPTIONAL EXAMPLE 2 (CAPSULE)

Following components were mixed and charged into geratin capsules in a conventional manner to prepare capsuled medicine.

| | |
|---|---|
| Compound of Example 1 | 1 (mg) |
| Corn starch | 107 |
| Lactose | 38 |
| Polyvinylpyrrolidone | 2 |
| Magnesium stearate | 2 |
| | 150 (mg/capsule) |

PRESCRIPTIONAL EXAMPLE 3 (TABLET)

Following components were mixed to prepare tablets in a conventional manner.

| | |
|---|---|
| Fumarate of Example 4 | 5 (mg) |
| Potato starch | 55 |
| Fine crystalline cellulose | 30 |
| Geratin | 8 |
| Magnesium stearate | 2 |
| | 100 (mg/tablet) |

PRESCRIPTIONAl EXAMPLE 4 (CAPSULE)

Following components were mixed and charged into geratin capsules in a conventional manner to prepare capsuled medicine.

| | |
|---|---|
| Fumarate of Example 4 | 5 (mg) |
| Corn starch | 106 |
| Lactose | 35 |
| Polyvinylpyrrolidone | 2 |
| Magnesium stearate | 2 |
| | 150 (mg/capsule) |

We claim:

1. A 1,4-dihydropyridine derivative represented by the formula

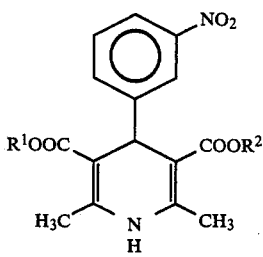

(I)

wherein one of $R^1$ and $R^2$ is $C_{3-6}$ cycloalkylmethyl group and the other is a group of

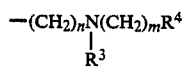

in which $R^3$ is hydrogen atom or lower alkyl group and $R^4$ is hydrogen atom, hydroxyl radical, carboxyl radical, alkoxycarbonyl group, carbamoyl radical or phenyl radical, unsubstituted or substituted by one or two halogens, lower alkoxy or nitro or trilower alkylsilyl group, and n and m are an integer of 1 to 6, respectively and a salt thereof.

2. A compound as claimed in claim 1, wherein said derivative is 3-cyclopropylmethyl 5-[2-(N-benzyl-N-methylamino)ethyl] 1,4-dihydro-2,6-dimethyl-4-(3-nitrophenyl)pyridine-3,5-dicarboxylate.

3. A compound as claimed in claim 1, wherein said derivative is 3-cyclopropylmethyl 5-[2-(N-dimethylamino)ethyl] 1,4-dihydro-2,6-dimethyl-4-(3-nitrophenyl)pyridine-3,5-dicarboxylate.

4. A compound as claimed in claim 1, wherein said derivative is 3-[2-[N-(4-chlorobenzyl)-N-methylamino]ethyl] 5-cyclopropylmethyl 1,4-dihydro-2,6-dimethyl-4-(3-nitrophenyl)pyridine-3,5-dicarboxylate.

5. A compound as claimed in claim 1 wherein said derivative is 3-cyclopropylmethyl 5-[2-[N-(4-methoxybenzyl)-N-methylamino]ethyl] 1,4-dihydro-2,6-dimethyl-4-(3-nitrophenyl)pyridine-3,5-dicarboxylate.

6. A compound as claimed in claim 1, wherein said derivative is 3-cyclopropylmethyl 5-[2-(N-methyl-N-trimethylsilylmethylamino)ethyl] 1,4-dihydro-2,6-dimethyl-4-(3-nitrophenyl)-pyridine-3,5-dicarboxylate.

7. A compound as claimed in claim 1, wherein said derivative is 3-[2-(N-carbamoylmethyl-N-methylamino)ethyl 5-cyclopropylmethyl 1,4-dihydro-2,6-dimethyl-4-(3-nitrophenyl)pyridine-3,5-dicarboxylate.

8. A compound as claimed in claim 1, wherein said derivative is 3-cyclopropylmethyl 5-[2-[N-(2,4-dichlorobenzyl)-N-methylamino]-ethyl] 1,4-dihydro-2,6-dimethyl-4-(3-nitrophenyl)pyridine-3,5-dicarboxylate.

9. A pharmaceutical composition comprising a vasodilating effective amount of a 1,4-dihydropyridine derivative of the formula

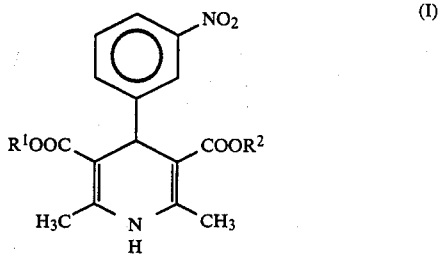

(I)

wherein one of $R^1$ and $R^2$ is $C_{3-6}$ cycloalkylmethyl group and the other is a group of

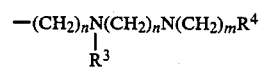

in which $R^3$ is hydrogen atom or lower alkyl group and $R^4$ is hydrogen atom, hydroxyl radical, carboxyl radical, alkoxycarbonyl group, carbamoyl radical or phenyl radical, unsubstituted or substituted by one or two halogens, lower alkoxy or nitro, or trilower alkylsilyl group, and n and m are integers of 1 to 6, respectively, or a pharmaceutically acceptable salt thereof, together with a pharmaceutically acceptable carrier.

10. A pharmaceutical composition as claimed in claim 9, wherein the 1,4-dihydropyridine derivative is at least one selected from the group consisting of
   (a) 3-cyclopropylmethyl 5-[2-(N-benzyl-N methylamino)ethyl] 1,4-dihydro-2,6-dimethyl-4-(3-nitrophenyl)pyridine-3,5-dicarboxylate,
   (b) 3-cyclopropylmethyl 5-[2-(N,N-dimethylamino)ethyl] 1,4-dihydro-2,6-dimethyl-4-(3-nitrophenyl)pyridine-3,5-dicarboxylate,
   (c) 3-[2-[N-(4-chlorobenzyl)-N-methylamino]ethyl 5-cyclopropylmethyl 1,4-dihydro-2,6-dimethyl-4-(3-nitrophenyl)pyridine-3,5-dicarboxylate, (d) 3-cyclopropylmethyl 5-[2-[N-(4-methoxybenzyl)-N methylamino]ethyl] 1,4-dihydro-2,6-dimethyl-4-(3-nitrophenyl)-pyridine-3,5-dicarboxylate,
(e) 3-cyclopropylmethyl 5-[2-[methyl-N-trimethylsilymethylamino)-ethyl 1,4-dihydro-2,6-dimethyl-4(3-nitrophenyl)pyridine-3,5-dicarboxylate,
(f) 3-[2-[N-carbamoylmethyl-N-methylamino)ethyl 5-cyclopropylmethyl 1,4-dihydro-2,6-dimethyl-4-(3-nitrophenyl)pyridine-3,5-dicarboxylate, and
(g) 3-cyclopropylmethyl 5-[2-[N-(2,4-dichlorobenzyl)-N-methylamino]-ethyl] 1,4-dihydro-2,6-dimethyl-4-(3-nitrophenyl)-pyridine-3,5-dicarboxylate, and
(h) a pharamaceutically acceptable salt of (a) to (g).

* * * * *